US009551329B2

(12) United States Patent
Cormier et al.

(10) Patent No.: US 9,551,329 B2
(45) Date of Patent: Jan. 24, 2017

(54) AUTOMATED DILUTION FOR LIQUID CHROMATOGRAPHY

(75) Inventors: Sylvain Cormier, Mendon, MA (US); Richard W. Andrews, Rehoboth, MA (US); Robert Tacconi, Medfield, MA (US); Craig H. Dobbs, Mendon, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 13/146,683

(22) PCT Filed: Feb. 17, 2010

(86) PCT No.: PCT/US2010/024387
§ 371 (c)(1),
(2), (4) Date: Oct. 14, 2011

(87) PCT Pub. No.: WO2010/099005
PCT Pub. Date: Sep. 2, 2010

(65) Prior Publication Data
US 2012/0103075 A1    May 3, 2012

Related U.S. Application Data

(60) Provisional application No. 61/156,040, filed on Feb. 27, 2009.

(51) Int. Cl.
*F04B 13/02* (2006.01)
*G01N 1/38* (2006.01)
(Continued)

(52) U.S. Cl.
CPC .............. *F04B 13/02* (2013.01); *G01N 1/38* (2013.01); *G01N 1/40* (2013.01); *G01N 30/20* (2013.01)

(58) Field of Classification Search
CPC ............ G01N 1/38; G01N 1/40; G01N 30/24; F04B 13/02
(Continued)

(56) References Cited

U.S. PATENT DOCUMENTS

| 4,036,062 A | 7/1977 | Cruzan |
| 4,620,452 A | 11/1986 | Seki |

(Continued)

FOREIGN PATENT DOCUMENTS

| CN | 85107185 A | 4/1987 |
| WO | WO 2007109157 A2 * | 9/2007 |

OTHER PUBLICATIONS

PCT International Search Report, Form PCT/ISA/220 /210 for PCT/US2010/024387 dated Apr. 21, 2010.
(Continued)

*Primary Examiner* — Hezron E Williams
*Assistant Examiner* — David Z Huang
(74) *Attorney, Agent, or Firm* — Waters Technologies Corporation

(57) ABSTRACT

Described are a method and system for diluting a sample in a liquid chromatography system. A sample flowing at a first flow rate is combined for a predetermined time with a diluent flowing at a second flow rate to generate a volume of diluted sample. The diluted sample has a dilution ratio determined according to the two flow rates. A portion of the volume is loaded into a sample loop of an injection valve and subsequently injected into a mobile phase flowing to a chromatography column. The method eliminates the need to have a technician available to perform dilutions or to transfer the sample to a remote location for dilution. Advantageously, manufacturing or processing downtime to perform the dilution is not required and the amount of sample flowing to waste is reduced.

21 Claims, 4 Drawing Sheets

(51) Int. Cl.
    *G01N 1/40*    (2006.01)
    *G01N 30/20*   (2006.01)

(58) Field of Classification Search
    USPC .............................. 73/61.55, 61.56; 417/313
    See application file for complete search history.

(56) References Cited

U.S. PATENT DOCUMENTS

| | | | |
|---|---|---|---|
| 4,882,781 | A * | 11/1989 | Allington ..................... 700/282 |
| 5,278,626 | A | 1/1994 | Poole et al. |
| 5,869,004 | A | 2/1999 | Parce et al. |
| 6,211,956 | B1 | 4/2001 | Nicoli |
| 6,357,306 | B1 | 3/2002 | Jaeger et al. |
| 6,475,441 | B1 * | 11/2002 | Parce et al. ................... 436/179 |
| 2004/0025575 | A1 | 2/2004 | Petro et al. |
| 2005/0037517 | A1 | 2/2005 | Anderson et al. |
| 2005/0194007 | A1 * | 9/2005 | Hagleitner ............... 128/200.23 |
| 2006/0127237 | A1 | 6/2006 | Shaw et al. |

OTHER PUBLICATIONS

PCT International Written Opinion, Form PCT/ISA/237 for PCT/US2010/024387 dated Apr. 21, 2010.
Chinese Office Action and Search Report for Application No. 201080009456.4, dated Oct. 14, 2013.
Extended European Search Report for Application No. 10746644.3, dated Sep. 16, 2016 (7 pages).

* cited by examiner

AUTOMATED DILUTION FOR LIQUID CHROMATOGRAPHY

CROSS REFERENCE TO RELATED APPLICATIONS

This application claims priority to and benefit of U.S. Provisional Application No. 61/156,040, filed Feb. 27, 2009, the contents of which are expressly incorporated herein by reference in their entirety.

FIELD OF THE INVENTION

The invention relates generally to liquid chromatography systems. More particularly, the invention relates to a method for conveniently and efficiently diluting a sample for injection into a mobile phase in a liquid chromatography system.

BACKGROUND OF THE INVENTION

High pressure liquid chromatography (HPLC) systems sometimes require that a sample be diluted before it is injected into the mobile phase flowing to a chromatography column. Various reasons exist for diluting the sample prior to injection. For example, a system may not be capable of injecting a sufficiently small quantity of sample (e.g., picoliters) to avoid a mass overload condition for the chromatography column. Alternatively, the native solvent containing the sample may be inappropriate for the stationary phase due to a physical property (e.g., pH level) of the solvent. In another example, the sample may be dissolved in a strong solvent that interacts with the stationary phase, leading to ambiguous results in the chromatogram.

Dilutions can be performed manually by a skilled technician; however, it is not always practical to keep a technician available to perform dilutions. In many instances, the technician and equipment for performing the dilution are located an inconvenient distance from the HPLC system. Significant delay can occur if the sample is transferred to a remote location for dilution, potentially resulting in manufacturing or processing downtime. Moreover, the additional inconvenience of tracking the transported sample is often necessary.

The present invention addresses the problems set forth above and provides additional advantages.

SUMMARY OF THE INVENTION

In one aspect, the invention features a method of diluting a sample in a liquid chromatography system. A sample flowing at a first flow rate is combined for a predetermined time with a diluent flowing at a second flow rate to generate a volume of diluted sample. The diluted sample has a dilution ratio responsive to the first and second flow rates. A portion of the volume is loaded into a sample loop of an injection valve and subsequently injected into a mobile phase flowing to a chromatography column.

In another aspect, the invention features a method of diluting a sample in a liquid chromatography system. A sample flowing at a first flow rate and a diluent flowing at a second flow rate are combined for a predetermined time to generate in a fluid channel a volume of diluted sample. The diluted sample has a dilution ratio responsive to the first and second flow rates. A portion of the volume is loaded into a sample loop of an injection valve. The injection valve is switched so that the sample loop is inserted into a channel for a mobile phase flowing to a chromatography column and the portion of the volume is thereby injected into the mobile phase.

In yet another aspect, the invention features a system for injecting a diluted sample in a liquid chromatography system. The system includes a sample source, diluent source, control module, fluid combiner and injection valve. The sample source and diluent source supply sample and diluent, respectively, during a dilution time. The control module is in communication with the sample source and the diluent source to control the first flow rate, the second flow rate and the dilution time. The fluid combiner has a first inlet port in communication with the sample source, a second inlet port in communication with the diluent source and an outlet port. The fluid combiner supplies a volume of a diluted sample through the output port during the dilution time. The injection valve has a sample loop and is in communication with the outlet port of the fluid combiner. The injection valve is configured to load a portion of the volume of the diluted sample into the sample loop during a loading time.

BRIEF DESCRIPTION OF THE DRAWINGS

The above and further advantages of this invention may be better understood by referring to the following description in conjunction with the accompanying drawings, in which like numerals indicate like structural elements and features in the various figures. For clarity, not every element may be labeled in every figure. The drawings are not necessarily to scale, emphasis instead being placed upon illustrating the principles of the invention.

DETAILED DESCRIPTION

In brief overview, the invention relates to a method of diluting a sample in a liquid chromatography system. A sample flowing at a sample rate and a diluent flowing at a diluent rate are combined for a certain time to generate a volume of diluted sample. A portion of the volume is loaded into a sample loop of an injection valve and subsequently injected into a mobile phase flowing to a chromatography column. The method reduces the amount of sample wasted in conventional dilution processes for liquid chromatography.

Figure 1:
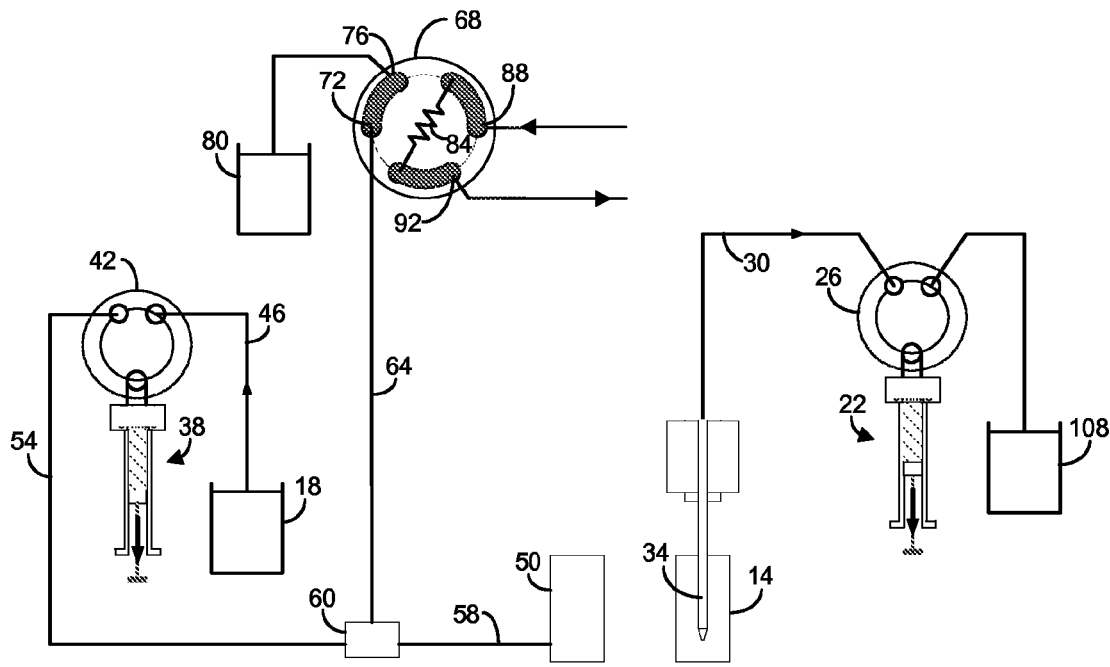
FIG. 1 is a schematic illustration of a portion of a liquid chromatography system according to an embodiment of the invention.

FIG. 1 is a schematic illustration of a portion of a liquid chromatography system according to an embodiment of the invention. The system includes a sample reservoir 14 and diluent reservoir 18. The sample reservoir 14 can be a vial or other container that holds a quantity of sample to be injected into a chromatography column (not shown) after dilution. Similarly, the diluent reservoir 18 can be a container that holds a quantity of diluent used to dilute the sample. The system also includes a sample syringe 22 that is coupled through a sample valve 26 and tubing 30 (or other fluid channel or conduit) to the sample reservoir 14. In the illustrated embodiment, the tubing 30 is coupled to a sample needle 34 that is positioned in the sample reservoir 14 when the sample is drawn into the tubing 30 although in other embodiments the sample needle 34 may be absent so that the tubing 30 is directly coupled to the sample reservoir 14. A diluent syringe 38 is coupled through a diluent valve 42 and tubing 46 to the diluent reservoir 18. The system also includes an injection port 50 configured to receive the sample needle 34 at certain times during a chromatography cycle as described in more detail below.

The diluent valve 42 and the injection port 50 are each coupled by tubing or other fluid channel 54 and 58, respectively, to a respective inlet port of a "tee" or other mixing component 60. An outlet port of the tee 60 supplies a diluted sample to an input port 72 of a six-port injection valve 68 through tubing or fluid channel 64. In general, the dilution ratio of the diluted sample provided to the injection valve 68 is determined according to the flow rates of the sample and the diluent at the tee 60.

Figure 2:
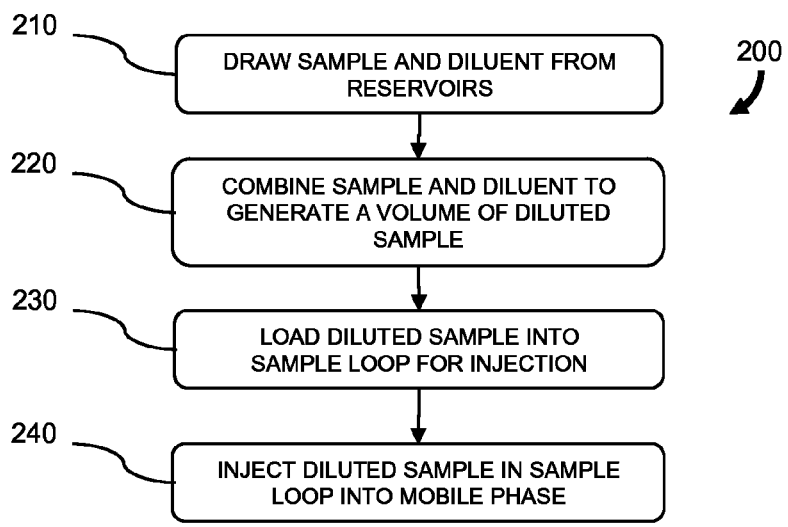
FIG. 2 is a flowchart representation of an embodiment of a method of diluting a sample in a liquid chromatography system according to the invention.

FIG. 2 is a flowchart representation of an embodiment of a method 200 of diluting a sample in a liquid chromatography system according to the invention. Referring also to FIG. 1, the sample and diluent valves 26 and 42 are initially configured so that the sample is drawn into holding loop 30 and diluent is drawn (step 210) into the syringe 38, respectively. Preferably, the sample syringe 22 starts at a minimum volume (i.e., "home") position and a quantity of sample is drawn into and through the sample needle 34 during a portion of the intake stroke. The volume of drawn sample is not sufficient to reach the sample syringe 22.

Figure 3:
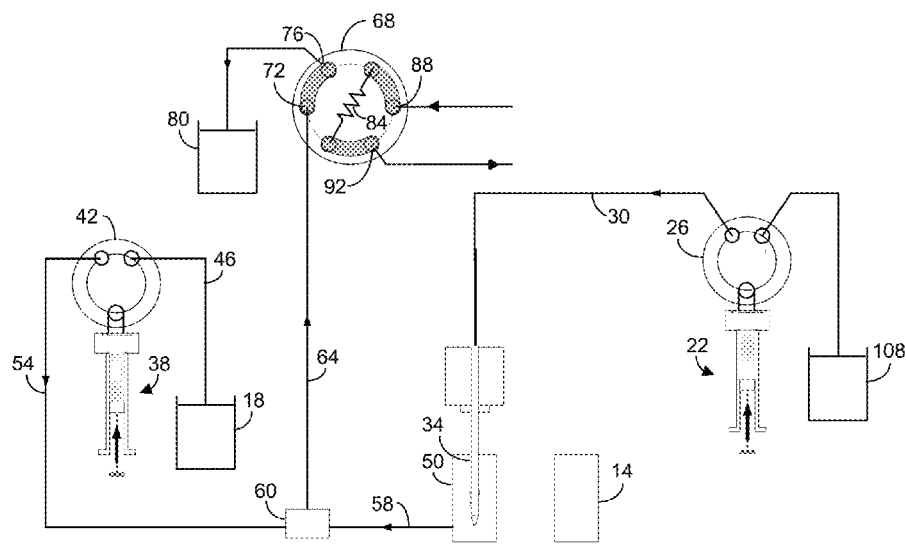
FIG. 3 is an illustration of the portion of the liquid chromatography system shown in FIG. 1 configured for dilution of a sample.

Subsequently, the needle valve 34 is removed from the sample reservoir 14 and positioned in the injection port 50 before starting dilution as shown in FIG. 3. The sample valve 26 and diluent valve 42 are configured so that the sample and diluent are pushed at a predetermined flow rate from their syringes 22 and 38, and combined (step 220) at the tee 60, yielding after a predetermined duration (i.e., a dilution time) a known volume of diluted sample in the tubing 64 connected to the tee outlet port. Since the sample syringe 22 was activated at its home position during the draw stage (FIG. 1) and because the sample syringe 22 is limited to a maximum of a single stroke during the dilution stage, only sample is pushed through the sample needle 34. The flow rates of the sample and the diluent are controlled to obtain the desired dilution ratio. For example, the syringes 22 and 38 can be operated by stepper motors under the management of a control module to generate the desired flow rates.

In many applications, the amount of sample and/or diluent available in the reservoirs 14 and 18 is limited. In addition, the sample, diluent or both sample and diluent may have special handling and disposal requirements. Thus it can be desirable to limit the amount of sample and diluent consumed during chromatography measurements. According to an embodiment of the invention, the time during which the syringes 22 and 38 push the sample and diluent is accurately controlled to ensure sufficient volume of diluted sample to fill the tubing 64 between the tee 60 and injection valve 68, and to pass through inlet and outlet ports 72 and 76, respectively, of the injection valve 68 while limiting the amount of diluted sample exiting to the waste 80.

The internal diameter of the tubing 64 is typically small (e.g., 6 inches of 0.005 inch tubing) and the pressure of the diluted sample flow is typically low (e.g., 20-30 psi). Thus sufficient time is allowed to lapse to ensure that the diluted sample fills the tubing 64 prior to loading the diluted sample into a sample loop 84 of the injection valve 68.

During the period when the diluted sample flow is established, the mobile phase flows under high pressure from a pump system (not shown) through a high pressure inlet port 88, sample loop 84 and high pressure outlet port 92 of the injection valve 68. The mobile phase exiting the high pressure outlet port 92 flows to the chromatography column.

Figure 4:
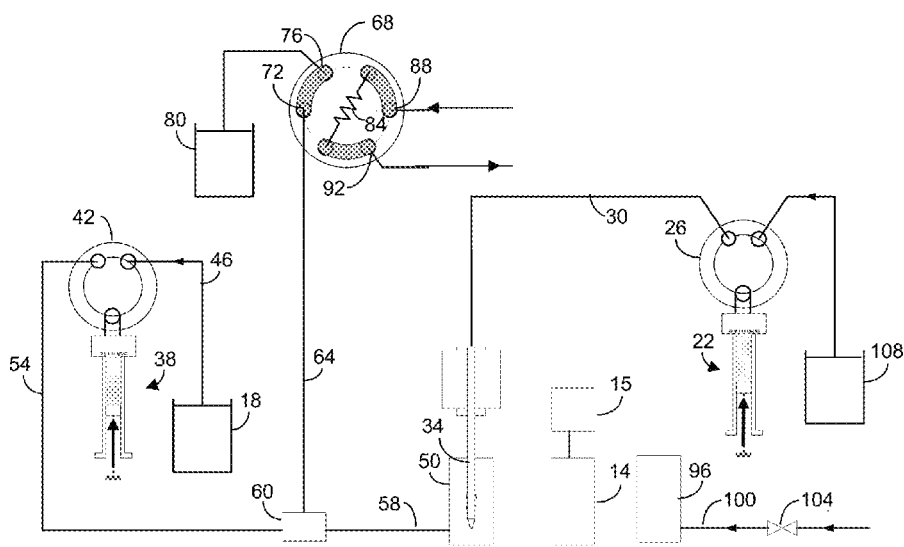
FIG. 4 shows an alternative embodiment to FIG. 3 that enables sampling of a flowing stream in a process line.

FIG. 4 shows an alternative configuration to FIG. 3 where a sampling port 96 is coupled to a process line through a conduit or fluid channel 100 that may include one or more control valves 104. This configuration enables sampling of a flowing stream in a process line. Samples can be drawn into the sample needle 34 at discrete times. Alternatively, samples can be taken from a slip stream (i.e., sample stream) in a process line. The sample reservoir 14 can be used to supply a standard for the chromatography measurements and can be used periodically between some or all of the sample stream measurements. Optionally, the sample or standard reservoir 14 is pressurized to at least partially compensate for pressure loss in the tubing. For example, the sample reservoir 14 can be a pressurized sample vial or pneumatic amplifiers 15 can be employed to increase the sample flowing from the reservoir 14.

Figure 5:
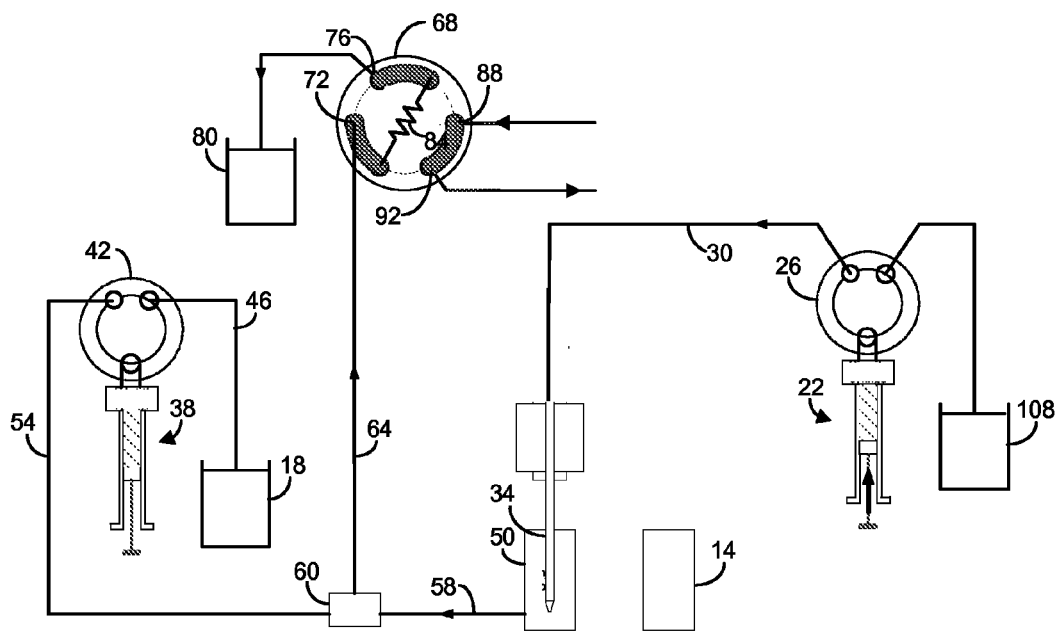
FIG. 5 is an illustration of the portion of the liquid chromatography system shown in FIG. 3 after configuring the injection valve in a load position.

To prepare the diluted sample for injection into the mobile phase, the injection valve 68 is temporarily configured from the position shown in FIG. 3 to a load position as shown in FIG. 5 so that the sample loop 84 is removed from the high pressure path for the mobile phase. During the load stage, the diluted sample is received at the inlet port 72 and flows through the sample loop 84 before exiting the injection valve 68 at the outlet port 76. Thus the diluted sample is loaded (step 230) into the sample loop 84 and is available for injection. During the load stage, at least one of the syringes 22 and 38 continues to push sample and/or diluent into the tee 60 and tubing 64. As illustrated, the sample syringe 22 continues to push sample while the diluent syringe 38 is disabled. This mode of operation may be preferred if the stepper motor control of the sample syringe 22 provides more accurate volume control than would otherwise be possible using stepper motor control of the diluent syringe 38, thereby enabling more accurate dispensing of the diluted sample to the injection valve 68. It should be appreciated that other modes of syringe operation can also be used during the load stage, such as operating only the diluent syringe 38 or simultaneous operation of both syringes 22 and 38.

The time during which the sample syringe 22 is active for loading the diluted sample into the sample loop 84 is carefully controlled to ensure that the entire volume of diluted sample in the tubing 64 is not passed to waste 80. If the duration is too long, the sample loop 84 is loaded with the solvent (e.g., sample) in the tubing 30 that was used to push the volume of diluted sample. Thus knowledge of the volume of the tubing 64 between the tee 60 and injection valve 68, and the flow rate of the diluted sample through the tubing 64 can be used to determine the proper duration and for synchronizing the activation times of the syringes 22 and 38 and the injection valve 68.

Figure 6:
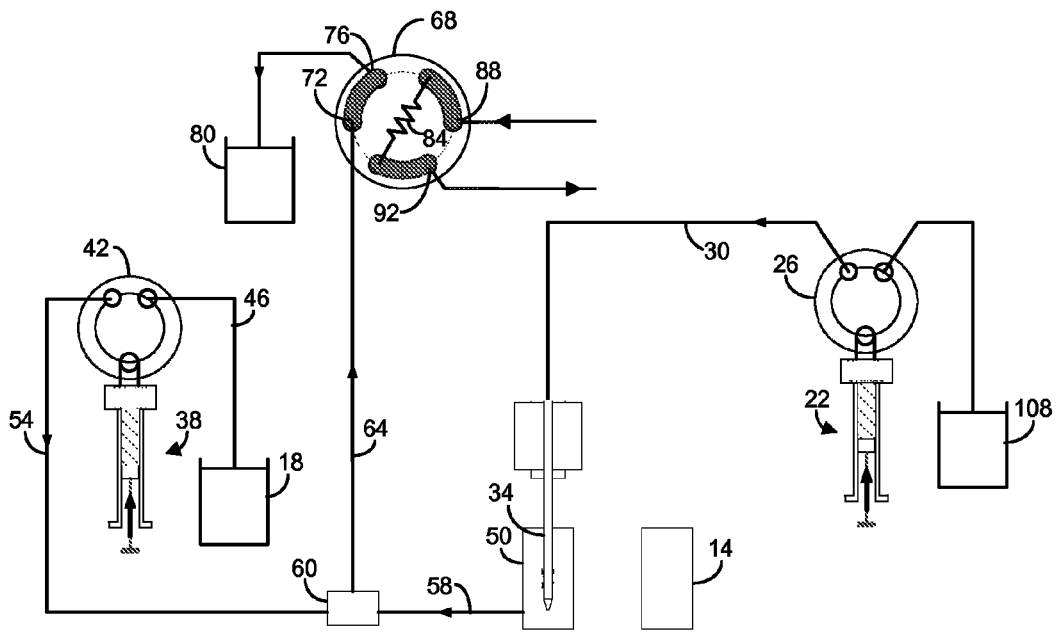
FIG. 6 is an illustration of the portion of the liquid chromatography system shown in FIG. 5 after configuring the injection valve in an inject position.

After loading is complete, the injection valve 68 is configured for injection as shown in FIG. 6 so that the high pressure mobile phase flows through the high pressure inlet port 88, sample loop 84 and high pressure outlet port 92 before passing to the chromatography column. Thus the diluted sample previously loaded into the sample loop 84 is injected (step 240) into the continuously flowing mobile phase.

Figure 7:
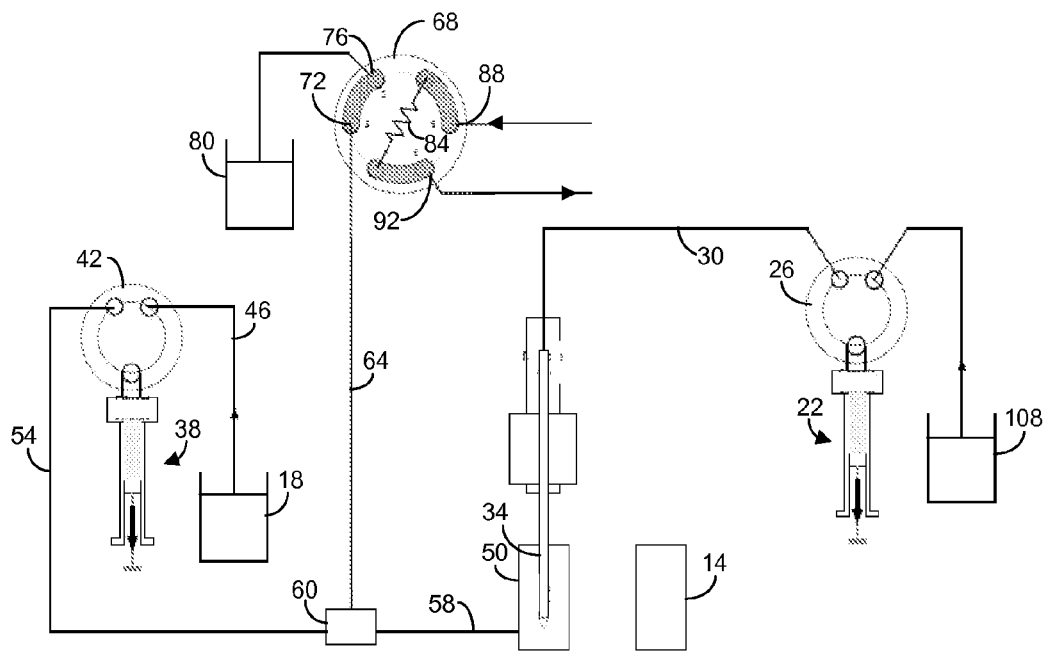
FIG. 7 illustrates a configuration of a portion of a liquid chromatography system during preparation for a wash stage.
Figure 8:
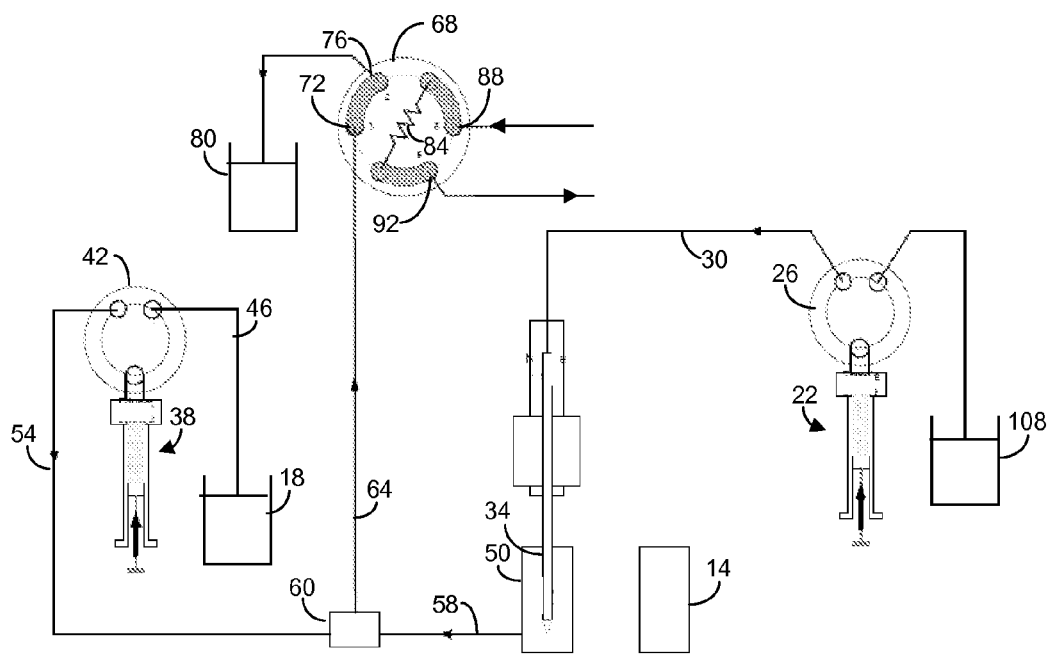
FIG. 8 illustrates the system of FIG. 7 during a wash stage.

FIG. 7 illustrates a configuration in which a wash solvent is drawn from a wash container 108 into the sample syringe 22. FIG. 8 shows how the wash solvent is pushed through the tubing 30 and sample needle 34. The particular wash solvent used is selected for its capability to dissolve any sample remaining in the sample needle 34. This process ensures that no sample remains in the sample needle 34 to contaminate a subsequent sample. In some instances where the next sample to be drawn is the same as the previous sample, the wash process can be omitted; however, in other instances it may be preferable to perform the wash.

A series of separations may be performed by the chromatography system to obtain a measurement average and to reduce the effect of measurement noise. In this instance the preparation of a diluted sample for each measurement cycle preferably occurs while the immediately preceding separation is performed.

Table 1 lists the mean sample detected (peak area counts), sample standard deviation and the standard deviation normalized to the mean expressed as a percentage (i.e., % RSD) for measurements based on six injections for each of six different dilution ratios. The sample is caffeine and the diluent is 90/10 $H_2O$/ACN (acetonitrile). The mean sample detected values exhibit a highly linear relationship with respect to the ratio of sample and diluent. A low value for normalized RSD is achieved for most dilution ratios and indicates that the dilution process is well controlled. At high dilution ratios, the relative flow rate for the sample is sufficiently small such that effects due to the discrete nature of the stepper motor driving the sample syringe 22 may be observed. Stated otherwise, the sample flow might not appear to be at a constant rate and can lead to greater variations from the desired dilution ratio. To reduce this effect, different system components can be utilized for different dilution ratio ranges.

TABLE 1

| DILUTIONRATIO | MEAN | STANDARD DEVIATION | % RSD |
|---|---|---|---|
| 2:1 | 289310.2 | 1458.0 | 0.50 |
| 5:1 | 112026.2 | 618.3 | 0.55 |
| 10:1 | 56608.1 | 352.9 | 0.62 |
| 50:1 | 10827.6 | 74.9 | 0.69 |
| 100:1 | 6951.8 | 127.7 | 1.84 |
| 200:1 | 3354.2 | 31.4 | 0.94 |

While the invention has been shown and described with reference to specific embodiments, it should be understood by those skilled in the art that various changes in form and detail may be made therein without departing from the spirit and scope of the invention as recited in the accompanying claims.

What is claimed is:

1. A method of diluting a sample in a liquid chromatography system, the method comprising:
    providing a diluent syringe configured to receive a diluent;
    supplying diluent from the diluent syringe at a first flow rate;
    providing a sample syringe configured to receive a sample;
    supplying sample from the sample syringe at a second flow rate using a single stroke of the sample syringe;
    combining for a predetermined duration the sample flowing at the second flow rate and the diluent flowing at the first flow rate to generate a volume of diluted sample having a dilution ratio responsive to the first and second flow rates;
    loading a portion of the volume of diluted sample into a sample loop of an injection valve by disabling one of the diluent syringe and the sample syringe while operating the other of the diluent syringe and the sample syringe; and
    injecting the portion of the volume of diluted sample in the sample loop into a mobile phase flowing to a chromatography column.

2. The method of claim 1 further comprising drawing the sample from a sample source and drawing the diluent from a diluent source.

3. The method of claim 1 further comprising drawing the sample from a flowing stream in a process line and drawing the diluent from a diluent reservoir.

4. The method of claim 1 further comprising drawing the sample from a slip stream for a process line and drawing the diluent from a diluent reservoir.

5. The method of claim 1, further comprising passing a first portion of the volume of diluted sample to waste.

6. A method of diluting a sample in a liquid chromatography system, the method comprising:
    providing a diluent syringe configured to receive a diluent;
    supplying diluent from the diluent syringe at a first flow rate;
    providing a sample syringe configured to receive a sample;
    supplying sample from the sample syringe at a second flow rate using a single stroke of the sample syringe;
    combining for a predetermined duration the sample flowing at the second flow rate and the diluent flowing at the first flow rate to generate in a fluid channel a volume of diluted sample having a dilution ratio responsive to the first and second flow rates;
    loading a portion of the volume of diluted sample in the fluid channel into a sample loop of an injection valve by disabling one of the diluent syringe and the sample syringe while operating the other of the diluent syringe and the sample syringe; and
    switching the injection valve to insert the sample loop into a channel for a mobile phase flowing to a chromatography column, wherein the portion of the volume of diluted sample is injected into the mobile phase.

7. The method of claim 6 further comprising drawing the sample from a sample reservoir and drawing the diluent from a diluent reservoir.

8. The method of claim 7 wherein at least one of the sample reservoir or the diluent reservoir is pressurized.

9. The method of claim 6 further comprising drawing the sample from a flowing stream in a process line and drawing the diluent from a diluent reservoir.

10. The method of claim 6 further comprising drawing the sample from a slip stream for a process line and drawing the diluent from a diluent reservoir.

11. The method of claim 6, further comprising passing a first portion of the volume of diluted sample to waste.

12. A system for injecting a diluted sample in a liquid chromatography system, comprising:
- a sample source coupled to a sample syringe, the sample syringe configured to supply a sample at a first flow rate using a single stroke of the sample syringe during a dilution time;
- a diluent source coupled to a diluent syringe, the diluent syringe configured to supply a diluent at a second flow rate during the dilution time;
- a control module in communication with the sample source and the diluent source to control the first flow rate, the second flow rate and the dilution time;
- a fluid combiner having a first inlet port in communication with the sample source, a second inlet port in communication with the diluent source and an outlet port, the fluid combiner supplying a volume of a diluted sample through the outlet port at a flow rate responsive to the first and second flow rates; and
- an injection valve having a sample loop and being in communication with the outlet port of the fluid combiner, the injection valve being configured to load a portion of the volume of the diluted sample into the sample loop during a loading time in response to flow from one of the sample syringe and the diluent syringe while the other of the sample syringe and the diluent syringe is disabled.

13. The system of claim 12 wherein the sample source comprises a sample reservoir and a sample syringe in communication therewith.

14. The system of claim 13 wherein the sample reservoir is pressurized.

15. The system of claim 13 further comprising a stepper motor coupled to the sample syringe and in communication with the control module, wherein the stepper motor is operated during the dilution time so that the sample is supplied at the first flow rate.

16. The system of claim 13 further comprising a pneumatic amplifier disposed between the sample reservoir and the sample syringe.

17. The system of claim 12 wherein the diluent source comprises a diluent reservoir in communication with the diluent syringe.

18. The system of claim 17 further comprising a stepper motor coupled to the diluent syringe and in communication with the control module, wherein the stepper motor is operated during the dilution time so that the diluent is supplied at the second flow rate.

19. The system of claim 12 wherein the sample source comprises a fluid channel in communication with a flowing stream in a process line, the fluid channel comprising at least one control valve in communication with the control module.

20. The system of claim 12 wherein the sample source comprises a fluid channel in communication with a slip stream for a process line, the fluid channel comprising at least one control valve in communication with the control module.

21. The system of claim 12, wherein the injection valve is further configured to pass a first portion of the volume of the diluted sample through the sample loop to waste.

* * * * *